United States Patent [19]
Nelson

[11] Patent Number: 5,174,299
[45] Date of Patent: Dec. 29, 1992

[54] THERMOCOUPLE-BASED BLOOD FLOW SENSOR

[75] Inventor: James P. Nelson, Shoreview, Minn.

[73] Assignee: Cardiac Pacemakers, Inc., St. Paul, Minn.

[21] Appl. No.: 743,805

[22] Filed: Aug. 12, 1991

[51] Int. Cl.$^5$ ............................................. A61B 5/02
[52] U.S. Cl. ........................... 128/692; 128/736; 73/202.5
[58] Field of Search ............... 128/691, 692, 713, 673, 128/662.06, 736; 73/202.5

[56] References Cited

U.S. PATENT DOCUMENTS

| | | | |
|---|---|---|---|
| 3,438,253 | 4/1969 | Kuether et al. | 128/692 |
| 3,466,742 | 9/1969 | Sinclair | 128/692 |
| 3,561,266 | 2/1971 | Auphan et al. | 128/692 |
| 3,589,360 | 6/1971 | Sinclair | 128/692 |
| 3,620,207 | 11/1971 | Sinclair | 128/692 |
| 4,004,576 | 1/1977 | Gähwiler et al. | 128/713 |
| 4,153,048 | 5/1979 | Magrini | 128/692 |
| 4,217,910 | 8/1980 | Khalil | 128/670 |
| 4,236,527 | 12/1980 | Newbower et al. | 128/692 |
| 4,240,441 | 12/1980 | Khalil | 128/692 |
| 4,319,483 | 3/1982 | Durham et al. | 73/204.15 |
| 4,354,504 | 10/1982 | Bio | 128/691 |
| 4,407,298 | 10/1983 | Lentz et al. | 128/713 |
| 4,419,999 | 12/1983 | May, Jr. et al. | 128/691 |
| 4,460,802 | 7/1984 | Benedict et al. | 136/230 |
| 4,576,182 | 5/1986 | Normann | 128/692 |
| 4,696,304 | 9/1987 | Chin | 128/673 |
| 4,730,623 | 3/1988 | Lee | 128/692 |
| 4,739,771 | 4/1988 | Manwaring | 128/691 |
| 4,785,823 | 11/1988 | Eggers et al. | 128/692 |
| 4,796,640 | 1/1989 | Webler | 128/736 |
| 4,813,280 | 3/1989 | Miller, Jr. et al. | 73/273 |
| 4,819,655 | 4/1989 | Webler | 128/713 |
| 4,841,981 | 6/1989 | Tanabe et al. | 128/692 |
| 4,901,734 | 2/1990 | Griffin et al. | 128/692 |
| 4,941,475 | 7/1990 | Williams et al. | 128/692 |
| 5,005,574 | 4/1991 | Fearnot et al. | 128/419 PG |
| 5,009,234 | 4/1991 | Alt | 128/692 |
| 5,121,749 | 6/1992 | Nassi et al. | 128/692 |

Primary Examiner—William E. Kamm
Assistant Examiner—George Manuel
Attorney, Agent, or Firm—Haugen and Nikolai

[57] ABSTRACT

A thermocouple-based cardiac blood flow sensor for allowing discrimination between physiologic rhythms and pathologic rhythms of the heart. The sensor is built on a cardiac catheter or lead from a union of two dissimilar metals. The thermocouple junction is radially activated by blood flowing past the junction while situated in a blood vessel such as the superior vena cava. Temperature differences measured at axially displaced sites are related to blood flow and blood velocity. The thermocouple-based blood flow sensor is easy to use and unobtrusive. A further feature incorporates electrodes whereby impedance plethysmography can be used to determine blood vessel cross-sectional area so that blood flow through vessels which change in size can be assessed.

8 Claims, 4 Drawing Sheets

THERMOCOUPLE-BASED BLOOD FLOW SENSOR

This invention relates to an improved method and apparatus for cardiac blood flow sensing and, more particularly, to a thermocouple-based device for achieving arrythmia detection for implantable defibrillators; rate setting means in rate adaptive pacemaking; improved cardiac output measurement; and peripheral blood flow measurement in medical diagnostic apparatus.

BACKGROUND OF THE INVENTION

Cardiac output or blood flow is one of the key indicators of the performance of the heart. Blood flow can be defined as volume of fluid flow per time interval. Fluid velocity is a function of flow area at the measurement site. Use of blood flow measurements allows discrimination between physiologic rhythms, such as sinus tachycardia, which is caused by exercise or an emotional response, and other pathologic rhythms, such as ventricular tachycardia or ventricular fibrillation.

Cardiac arrythmia is defined as a variation of the rhythm of the heart from normal. The cardiac heartbeat normally is initiated at the S-A node by a spontaneous depolarization of cells located there during diastole. Disorders of impulse generation include premature contractions originating in abnormal or ectopic foci in the atria or ventricles, paroxysmal supraventricular tachycardia, atrial flutter, atrial fibrillation, ventricular tachycardia and ventricular fibrillation. Ventricular arrhythmia can occur during cardiac surgery or result from myocardial infarction. Ventricular tachycardia presents a particularly serious problem because the patient, if left untreated, may progress into ventricular fibrillation.

Blood flow measurements allow discrimination between normal and pathologic rhythms by providing a correlation between the electrical activity of the heart and the mechanical pumping performance or fluid flow activity of the heart. During sinus tachycardia, an increase in heart rate will usually be accompanied by an increase in cardiac output or blood flow. During ventricular tachycardia or ventricular fibrillation, heart rate increase will be accompanied by a decrease in, or perhaps a complete absence of, cardiac output or blood flow. A number of important cardiac and clinical devices may be improved by a more accurate measure of cardiac output. The ability to measure blood flow can be applied to the following four areas: (1) automatic implantable defibrillators, (2) rate adaptive pacemakers, (3) cardiac output diagnostic instruments and (4) peripheral blood flow instruments.

Prior art methods of measuring blood flow have included blood thermal dilution, vascular flow monitoring, and injectionless thermal cardiac output. U.S. Pat. No. 4,785,823 to Eggers, et al., which is incorporated herein by reference, teaches a thermal dilution catheter utilizing a pair of spaced electrodes in electrical contact with blood flowing adjacent to a catheter. In accordance with that patent, a potential difference is applied across the electrode which causes electric current to flow in the volume of blood in the region of the electrode, thereby creating a bolus of blood at elevated temperature suitable for measurement of blood flow by the thermal dilution principle. The device heats the blood by passing an electrical current between two or more electrodes, each of which is an electrical contact with the blood. The electrodes are mounted on a catheter or other similarly longitudinal support member which is inserted longitudinally in the blood vessel in which blood flow is to be measured. An AC electrical potential difference is applied to the electrodes. A temperature sensor is located in the blood stream downstream from the electrodes by being mounted on the support member. The temperature sensor produces an output indicative of the temperature of the blood adjacent to the sensor. This output is proportional to a conventional thermal dilution curve and provides an accurate measurement of the rate of blood flow between two spaced locations. The Eggers, et al. invention heavily depends on the fact that blood has a lower electrical resistance and, thus, the current will not take a path through proximally adjacent tissue. The device is intended for use as an insertable device that is fed into the right atrium, right ventricle and into the pulmonary artery. A device incorporating this invention was constructed but used an energy pulse of 100 volts RMS at 1 amp RMS at a frequency of 200 to 500 KHz for a duration of 2.5 seconds.

In U.S. Pat. No. 4,419,999 to James W. May, Jr., et al., incorporated herein by reference, there is described a method and apparatus for monitoring vascular flow wherein the device measures blood flow through a blood vessel utilizing the principle of energy conversion to heat by myocardial activity, organ metabolism, and laminar frictional flow in blood vessels. The device measures heat dissipation through the vessel wall with an obstruction to flow. The device is placed next to the vessel wall and an output signal correlates blood flow with temperature. The device is used in repaired vessels to study blood flow. The device's leads are brought through the skin and attached to a temperature monitor. It works by measuring the temperature of blood vessels both proximal and distal to an anastomotic repair. This is done by measuring temperatures that exist ambiently within the body on a continual basis by providing heat to the system and noting the rates of dissipation proximal and distal to the anastomotic repair. The device includes a thermal sensor which may be placed over a portion of the blood vessel with leads taken out transcutaneously to a temperature monitor.

Another U.S. Pat. No. 4,819,655 to William E. Webler, describes a method and system using a catheter which is configured such that fluid can circulate around it when the catheter is in position. The fluid may circulate down one lumen as far as the right atrium or ventricle over to another lumen and back up and out of the catheter. In using that invention, a solution is not injected into the blood stream. The catheter temperature sensor is positioned to monitor mixed venous blood temperature. A temperature sensing device monitors a fluid temperature at the inlet and outlet from the catheter. After steady state fluid circulation is initiated, a circulatory fluid cools the blood through the lumen walls. It also cools any adjacent fluid to the lumen which also cools the blood through the lumen wall and through dilution of heat introduced by the IV solution. An appropriate heat balance equation allows the cardiac output to be calculated. The method has a duty cycle and utilizes an equilibrium/disequilibrium measurement cycle.

In U.S. Pat. No. 4,865,036 to Chirife, entitled "Antitachyarrhythmia Pacemaker Using Pre-Ejection To Distinguish Physiologic From Pathologic Tachycardia," a cardiac apparatus for cardioversion or defibrillation is provided while, in the event of pathologic tachycardia or ventricular fibrillation, the rate of heart depolarization is compared to a predetermined heart rate value indicative of the onset of tachycardia. The heart's pre-ejection period is monitored to determine whether an increase in heart rate above the predetermined value is accompanied by a decrease in the pre-ejection period. If not, a pathologic rather than physiologic episode is diagnosed and a cardioversion pulse protocol is initiated. By also monitoring the mechanical pulse of the heart, ventricular fibrillation is diagnosed and the cardioverters prepare to shock the heart back into sinus rhythm. The mechanical pulse rate tracks the electrical rate of depolarization and tachyrhythmia is confirmed. The diagnosis may be further confirmed by taking into account the rate at which the heart rate increases.

The Sekii, et al. U.S. Pat. No. 4,979,514 entitled "Cardiac Output Measurement Method And System For The Application Of Same" relates to blood flow measurements, but differs from the present invention in that it incorporates a blood flow velocity measurement device with a cardiac output device and, as such, it is not applicable to an implantable arrangement. In addition, the method described in the Sekii, et al. patent for measuring blood velocity is different from the method outlined in that path.

The present invention differs substantially from the prior art in many respects. Initially, the invention is implantable, long-term, in a patient by way of a catheter. Further, continuous measurements of intravenous blood flow are possible with the invention. The present invention utilizes an extremely low-power solution. Moreover, the invention is unobtrusive and does not require the use of auxiliary terminals, fluids, catheters or lumens to measure the performance of the heart.

The novel blood flow sensor of the present invention is based on heat transfer principles. The heat induced into a fluid stream is carried away by the fluid via convection. The heat flow from the point of heat introduction to a downstream sensing position can be detected as a temperature difference between the two positions. Heat flow is then inversely proportional to the temperature difference between the two points. Heat flow can then be converted directly to fluid flow by knowing the thermal properties of the fluid and the dimensions in which the flow takes place. Prior art radially activated thermocouple elements have been designed for measurements of flow within a pipe. A good example of a radially activated thermocouple can be found in U.S. Pat. No. 4,460,802 to Paul Beckman which is incorporated herein by reference.

Present generation automatic implantable cardiac defibrillators or AICD devices have difficulty discriminating between the physiologic rhythms and pathologic rhythms of the heart. This limitation is due to the fact that electrical activity of the heart is used for detection of ventricular tachycardia or ventricular fibrillation rather than a mechanical indicator such as blood flow. Improper discrimination between the electrical and mechanical activity of the heart causes an incorrect interpretation of physiologic need.

Prior art rate-responsive pacemakers use various types of sensors to detect the exercise level or emotional response of the patient. Sensors presently employed include activity sensors, right ventricular impedance for measurement of pre-ejection interval or stroke volume, right ventricular temperature, q-t interval, evoked response gradient potential and other rate responsive methods. Rate responsive pacemakers are often programmed to convert the sensor signal to an appropriate pacing rate modifying signal. Certain parameters of the rate response algorithm, such as the rate slope and maximum pacing rate, are programmable and set up by the physician at implant and during the follow-up.

One limitation of present generation rate responsive pacemakers is that appropriate values for the foregoing parameters are often difficult to determine and, in fact, change over time. One of the goals for a pacemaker is to increase cardiac output by increasing pacing rate. However, as pacing rate increases past a certain point, cardiac output will begin to decrease due to factors such as inadequate ventricular filling. Appropriate pacing rates vary from patient to patient and can change for a given patient over time. The result is that in many cases, rate responsive pacemakers raise the pacing rate to inappropriately high levels. This causes less than optimum cardiac output for the level of activity and physical state of the patient.

Cardiac output and peripheral blood flow sensors are important devices used in various clinical procedures. The most common method for the measurement of cardiac output in the clinical practice today is thermal dilution. Here, a catheter equipped with a thermistor for temperature measurement and an injection port for administration of a saline solution is placed in the heart such that the thermistor is located in the pulmonary artery and the ejection port of the catheter is located in the right atrium. To measure cardiac output a volume of chilled saline is injected into the right atrium. As the chilled saline flows past the thermistor a temperature decrease is detected. The resulting signal is processed to yield blood flow rate information. The technique of thermal dilution has a number of significant disadvantages. Primarily, the greatest disadvantage is that continuous measurement of cardiac output is not possible. Only intermittent values can be determined due to the requirement of chilled saline injection. Secondly, the method is very sensitive to operator technique and this limits the accuracy inherently. A risk of infection is also introduced, given the fact that a foreign liquid is injected into the body.

OBJECTS

Thus, it is a principal object of this invention to provide a means whereby blood flow measurements can be employed to allow a more accurate method of discrimination between physiologic rhythms, such as sinus tachycardia, and pathologic rhythms, such as ventricular fibrillation, for use in implantable cardioverter defibrillators.

It is a further object to provide a means whereby blood flow can be used as a means of setting the appropriate pacing rate in rate responsive pacemakers.

It is a further object of this invention to provide a method of more accurately measuring cardiac output on a continuous basis.

Finally, it is an object of this invention to provide a method of measuring peripheral blood flow, by eliminating the need for mixing of the indicator and blood which exists when thermodilution methods are used to measure flow.

SUMMARY OF THE INVENTION

The invention provides a means of measuring blood flow by using a temperature difference method. A pair of radially activated thermocouple sensors is installed on a catheter (or alternatively on a pacing or defibrillator lead) which is placed in the blood flow. Located adjacent to the downstream thermocouple is an integral heater which provides a source of heat to raise the temperature of the flowing blood. The temperature difference between the thermocouples can be correlated with blood velocity. Knowing the geometric details (area) of the lumen of the vein or artery in which the sensor is disposed enables the calculation of fluid flow.

BRIEF DESCRIPTION OF THE DRAWINGS

To illustrate the invention, a preferred embodiment thereof will be described hereinafter with reference to the accompanying drawings. The preferred embodiment concerns a thermocouple-based blood flow sensor for the determination of fluid flow in veins and arteries.

DESCRIPTION OF THE PREFERRED EMBODIMENT

Blood flow, or cardiac output, is a primary indicator of performance of the heart. Cardiac output is defined as the product of stroke volume and heart rate and can be determined by measuring the blood flowing in the pulmonary artery. As mentioned above, the ability to measure blood flow has many applications including automatic implantable cardiac defibrillators (AICD), rate adaptive pacemakers, cardiac output instrumentation and peripheral blood flow instruments. The novel blood flow sensor of this invention is based on heat transfer principles. Generally, heat induced into a fluid is carried away by the fluid via convection. The heat flow from the point of heat introduction in the fluid to a downstream sensing position can be detected as a temperature difference between the two positions. The measured temperature difference can be related to the heat flow between the two points. Heat flow can then be converted directly to fluid flow by relating the thermal properties of the fluid to the dimensions in which the flow takes place.

More particularly, the present invention utilizes a combination of two radially activated thermocouple junctions, one of which is exposed to a heating element to measure blood flow in a blood vessel by detecting a temperature change between the junctions caused by the presence of the heat introduced into the blood by the heating element. The temperature difference is inversely proportional to velocity of blood flow carrying away the heat by way of thermal conduction.

Those skilled in the art will appreciate that the above method is accurate to measure flow only if the cross-sectional area of the blood vessel is constant during the measurement interval. As long as the cross-sectional area of the blood vessel remains constant, the thermocouple-based flow sensor can be calibrated to measure flow in terms of liters per minute. If, however, the cross-sectional vessel area changes, it is necessary to detect these changes so that flow can be obtained by multiplying a velocity signal and the appropriate area signal.

Figure 1:
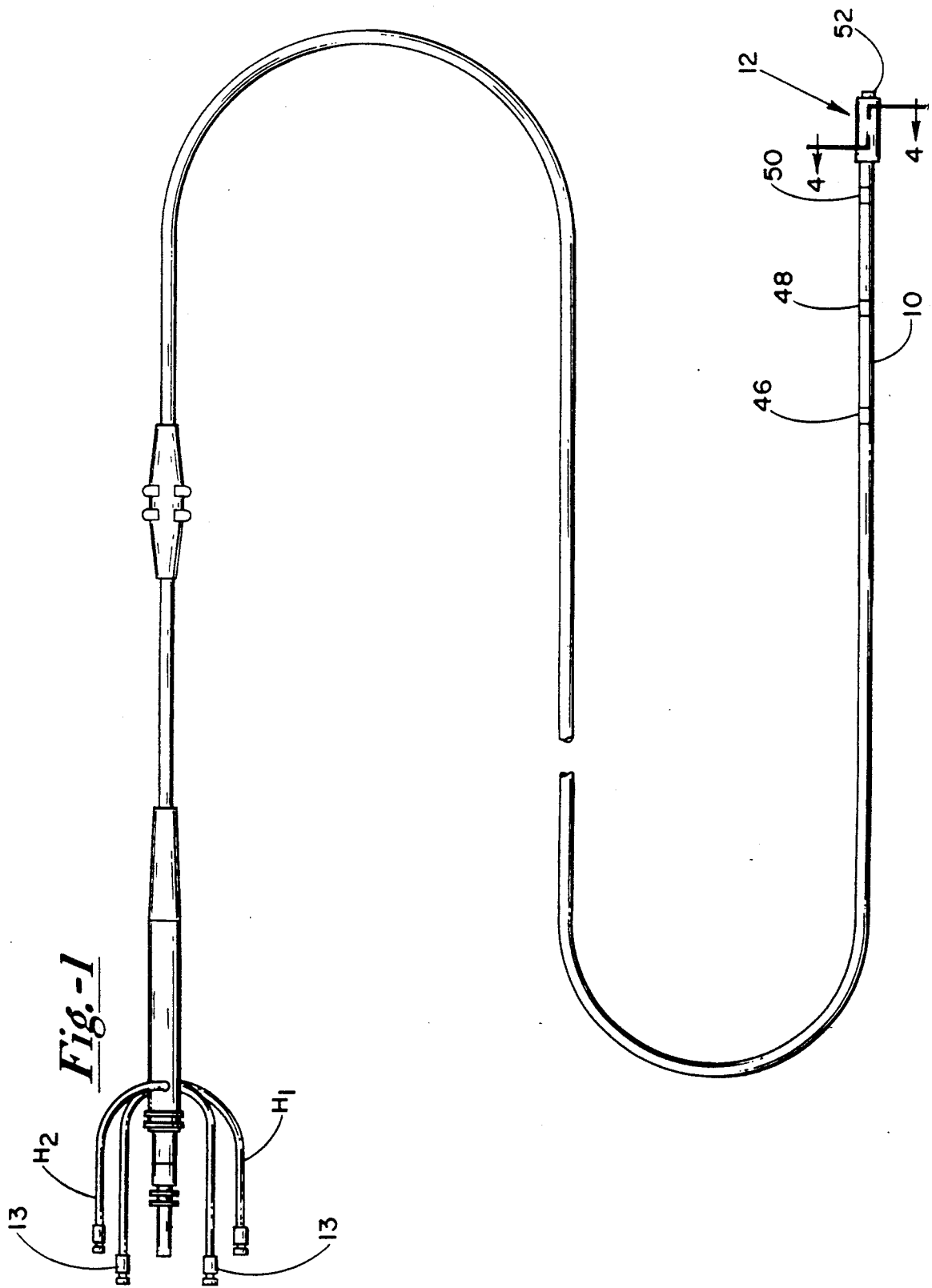
FIG. 1 shows a diagram of a cardiac catheter embodying the blood flow sensor of the present method of the invention.

FIG. 1 shows the apparatus of the invention positioned on a catheter. It is understood that this sensor could also be incorporated into existing pacemaker or defibrillator leads. The thermocouple-based blood flow sensor is identified by numeral 12 and is positioned on the catheter 10 such that it forms a non-obtrusive sensing element. It can be seen from FIG. 1 that the overall dimension of the sensor 12 is well within the aspect ratio of the catheter 10. The positioning of the sensor 12 allows the advantageous measurement of fluid flow in that the blood flow sensor does not have a tendency to rest along the leads or arterial surface but instead tends to be positioned clearly within the flow of blood. This provides a measure of fluid sensing in the mainstream rather than stagnant areas of venous or arterial flow. A number of different thermocouple configurations are possible for locating the temperature sensors and heating element and the embodiment of the invention shown in FIG. 1 is by way of example and not limitation.

Figure 2:
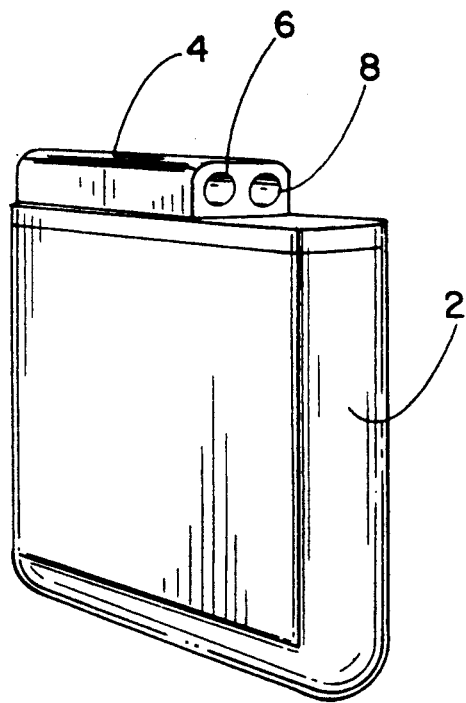
FIG. 2 shows an implantable cardiac rhythm management device with which the present invention may be used.

FIG. 2 is an implantable cardiac rhythm management device with which the present invention can be used. It includes a can 2 formed from a body compatible material which houses the cardiac stimulating circuitry (not shown). Affixed to the top of can 2 is a connector block 4 having a plurality of female terminal jacks 6 and 8 for receiving the male terminal pins of the lead 10. The circuitry may comprise an AICD in which blood flow is used as an indicator of the pathologic or physiologic state of the heart for determining the need for a defibrillating shock. Alternatively, the circuitry may comprise a rate adaptive bradycardia pacer or an antitachycardia pacer of known design.

Figure 3:
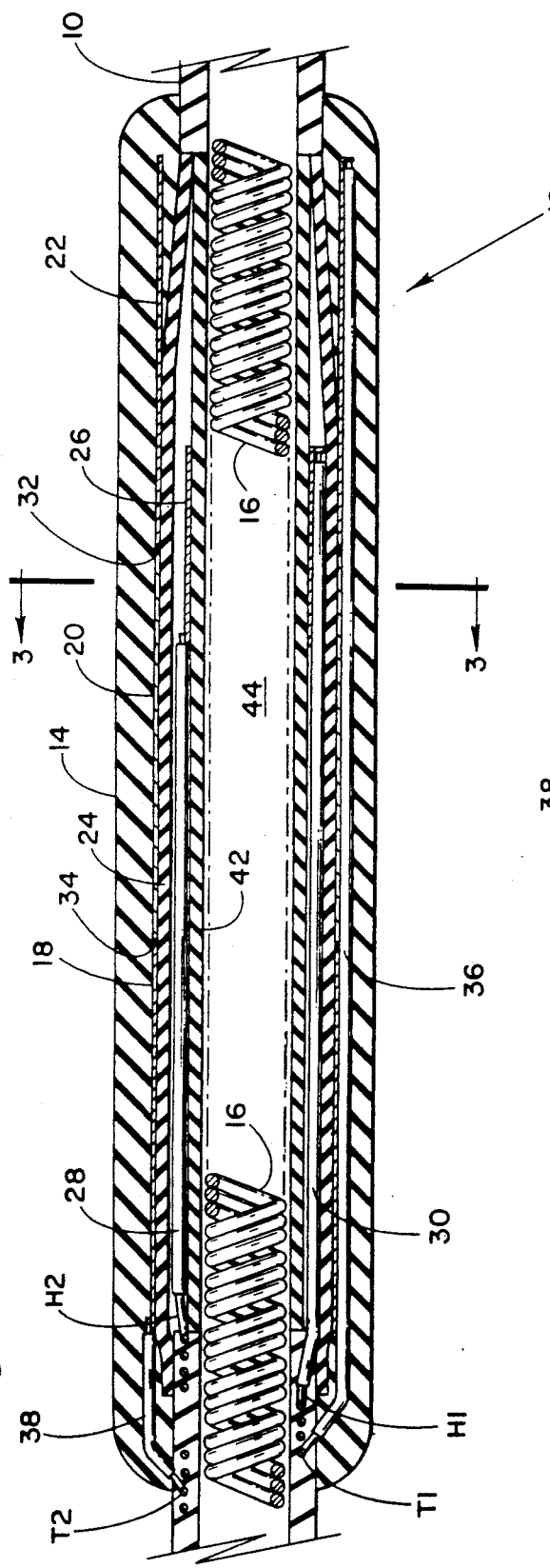
FIG. 3 shows an exploded cross-sectional diagram along the axis of the thermocouple-based blood flow sensor of FIG. 1.

FIG. 3 is a greatly enlarged longitudinal cross sectional diagram of the blood flow sensor 12 of FIG. 1. The sensor body is encased in a suitable insulator such as silicon rubber insulator 14 which surrounds and encloses the sensor from the blood. The contacts to the thermocouple sensors embedded in the silicon rubber body 14 are shown at T1 and T2. The two dissimilar metals comprising the thermocouple are shown as metal tubes 18, 20 and 22 which are positioned alternately along the length of the segment 100 to form the junctions 34 and 32 therebetween. Tubes 18 and 20 are of the same metal but differ from the metal of tube 22. The thermocouple elements are insulated from connecting wires and the catheter lead 10 by a further silicon insulation layer comprising tube 24.

An integral resistive heating element 26 is shown as positioned beneath the conductive heater leads 28 and 30 and underneath the silicon tubing insulation 24. The heating element 26 is powered by an appropriate voltage, either AC or DC, applied at connections H1 and H2 which provide a heating current to opposite ends of the heating element 26 via leads 28 and 30. The heater is positioned in this embodiment of the invention so as to span the junction 32 between thermocouple elements 20 and 22. It is sufficient that the heater provide an integral source of heating at junction 32 to form the thermal differential between junctions 32 and 34. The signal from junction 32 is fed via insulated wire 36 to a connection point T1 and a signal from junction 34 is fed via wire 38 to connection point T2. The signal across connectors T1 and T2 reflect the temperature difference between the two junctions caused by the heating element located adjacent to thermocouple junction 34.

The use of thermocouples for the sensing of temperature is well known in the art. The invention utilizes a unique, radially activated thermocouple configuration to provide faster and more sensitive temperature response when placed in the fluid stream for blood flow measurements in the body. Having described the structure of the apparatus of the invention, the function of the invention will now be described.

Figure 4:
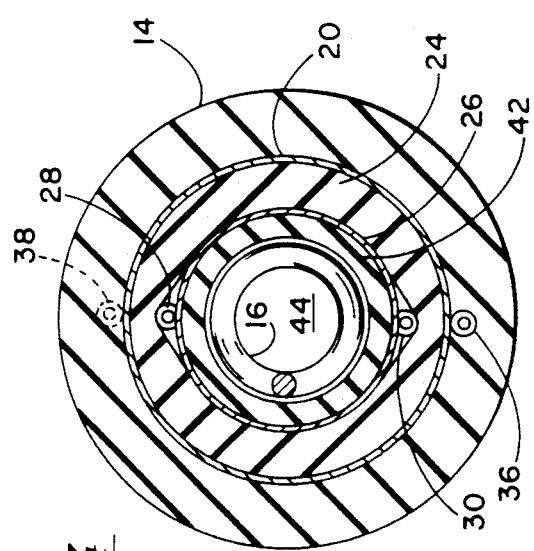
FIG. 4 shows a radial cross-section of the thermocouple-based blood flow sensor in accordance with the invention.

FIG. 4 shows a radial cross section of the thermocouple-based blood flow sensor as employed in one embodiment of the invention. In FIG. 4 the elements of the sensor can be clearly seen with the outer silicon rubber insulation 14 surrounding the entire sensor and the catheter conducting coils 16 for sensing cardiac activity and/or applying stimulating pulses to cardiac tissue 40 are in the center. Moving one layer in, the conductive leads 30 and 38 are shown situated within the silicon rubber insulation 14 and positioned around the thermocouple comprising segments 18, 20 and 22. The tubular thermocouple layer completely surrounds the catheter tube on which the sensor 12 is mounted and provides complete 360° radial sensing of thermal blood properties. With reference again to FIG. 3, beneath the thermocouple layer 22 is another insulating tubing layer 24 which provides insulation from the catheter or stimulating lead upon which the temperature sensor is situated. Beneath the insulating tubing 24 is the heating element layer 26 which is insulated from the cardiac catheter 10 by additional insulating tubing 42. Next, in the center lumen 44 is the trifilar catheter conducting coil 16 leading to the stimulating/sensing electrodes 46, 48, 50 and 52 (FIG. 1).

Figure 5:
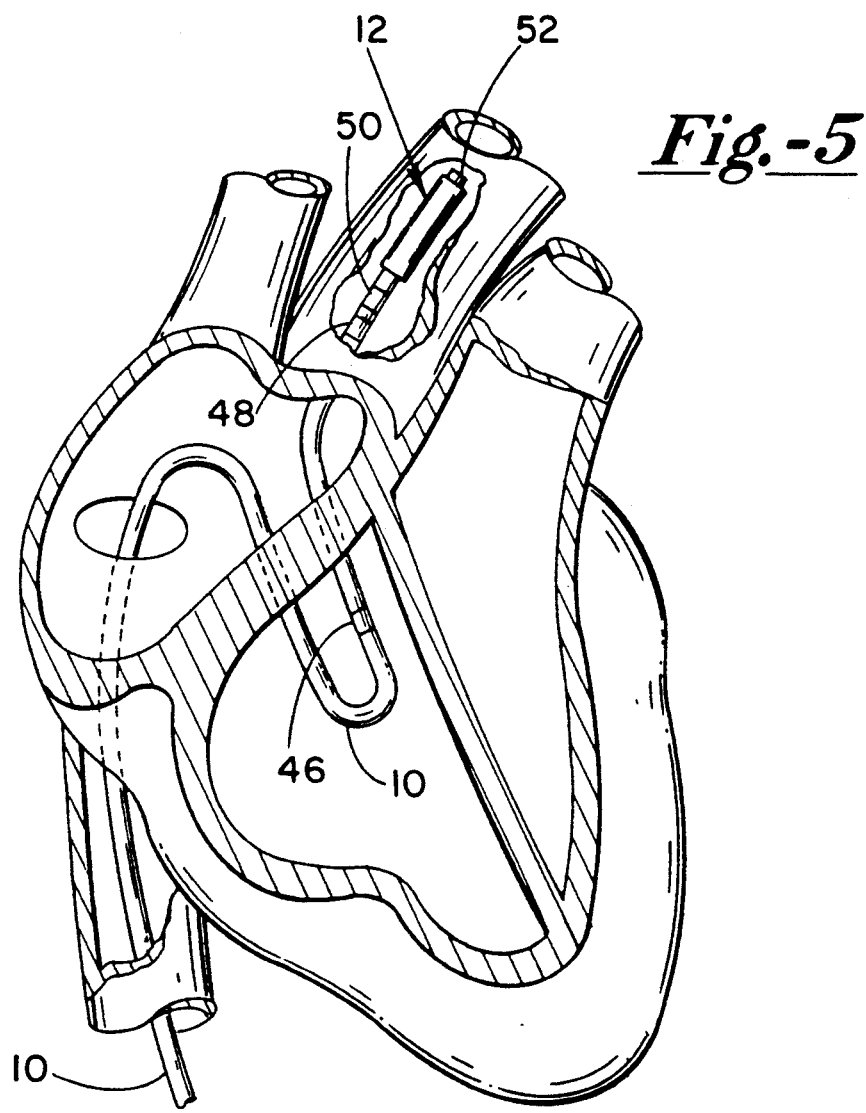
FIG. 5 shows a schematic of the thermocouple-based blood flow sensor installed in the pulmonary artery.

FIG. 5 shows a cut-away section of the heart with the apparatus of the invention installed such that the catheter 10 passes through the inferior vena cava into the right atrium and from there, the catheter is routed so that the blood flow sensor 12 of the invention is positioned in the pulmonary artery. Those skilled in the art will appreciate that being located in the pulmonary artery the blood flow sensor of the invention is adequately suited for measuring the cardiac output of the heart.

The catheter containing the blood flow sensor might also typically be inserted in the subclavian vein and advanced from that site to the appropriate location in the superior vena cava, depending on the application. Other approaches and locations are possible.

Referring again to FIG. 3, terminals T1 and T2 are separately connected, via helical conductors which extend the length of the lead body, to proximal connectors as at 13 (FIG. 1). The voltage measured across conductors T1 and T2 is proportional to the temperature differences between the junctions. For example, copper constantine type "T" thermocouple metals are a common combination used in the fabrication of thermocouple junctions designed to measure temperatures in the range of 37° C. (body temperature). The heating element 26 is in proximity to the junction 32 located distally of junction 34. Heat applied via the heating element 26 will be transferred to junction 32, causing a temperature rise relative to junction 34. Heat is also transferred to the blood stream in which sensor 12 is immersed and will be carried away by convection as blood flows past the sensor. The heat carried away by the blood is represented by a temperature difference between junctions 34 and 32. The rate of blood flow past the thermocouple and heater location is related to the thermal properties of the sensor materials and of the blood. In this configuration an increase in blood flow will result in a smaller temperature difference across the two junctions 34 and 32. A decrease in the blood flow will result in a higher temperature difference between the two junctions.

As mentioned earlier, accurate assessment of blood flow is dependent upon the cross-sectional area of the blood vessel in which the flow is being measured. If the size of the vessel can change during the measurement interval, some method must be available for assessing the area. Referring to FIG. 1, the catheter or lead of the present invention may also include a series of ring electrodes 46, 48 and 50, allowing the technique referred to as impedance plethysmography to be used in assessing the cross-sectional area. As is fully explained in the Salo, et al. U.S. Pat. No. 4,686,987 assigned to applicant's assignee, if an alternating current carrier signal is applied across a volume of blood such as the blood present between the tip electrode 11 and the proximal electrode 46, the resistance of the blood in which the sense electrodes 48 and 50 are immersed can be measured. Knowing the impedance value and the resistivity of blood as well as the distance between the electrodes 48 and 50, it is possible to compute the cross-sectional area using the well-known equation:

$$R = \rho \frac{l}{A}$$

Thus, a lead configured as illustrated in FIG. 1 allows measurement of both blood velocity and area, allowing flow to be computed. It is understood that other combinations are possible.

The invention minimizes the amount of heat required to produce a detectable temperature difference between junctions 34 and 32. The minimal heat capability will meet the energy constraints of implantable devices. Typically implantable devices have a requirement that energy consumption be very low so that the life time of the implant is high. In one embodiment, the device of the present invention is estimated to operate at about one milliwatt of power. This power consumption results in a current of about 166 microamps from a 6 volt battery system. One feature of the invention is that it can be used with a stimulator in which maximum power draw is needed only when certain heart rates are detected, otherwise the temperature sensing device remains in a standby or idle mode.

For example, assume that the sensor is activated for 3 minutes each time the patient's heart goes above some upper rate criteria. This will result in a total of 0.18 joules of energy expended for the three minutes to heat the sensor. This energy level is compatible with implantable systems and, in fact, is significantly less than the energy required to defibrillate the heart.

The temperature sensor/heater combination also yields superior performance. Only one milliwatt of power applied to the sensor is needed to result in a temperature difference in the order of 0.6° C. If type T thermocouples are used, this would mean a voltage of roughly 24 microvolts is developed across terminals T1 and T2. Those skilled in the art will appreciate that the change in temperature is inversely proportional to the square root of velocity of blood.

To illustrate the method of the invention, an example will now be given as to how much voltage change will occur for a given temperature change. Assume an initial condition which results in 0.6° C. of heat differential when a one milliwatt signal is applied to the heater. Assume also that at the onset of fibrillation, blood flow decreases from 5 liters per minute to 1 liter per minute. This results in an increase in temperature from 0.6° C. to 1.34° C. across the junction. A voltage change of approximately 30 microvolts is generated which can easily be detected.

The apparatus of the invention is biocompatible with human tissue. The sensor elements may advantageously be placed in a lead which may suitably be coated with a medical grade plastic material that is well known in the art. For example, materials such as silicon or polyurethane have well known biocompatibility characteristics and will eliminate biocompatibility problems. The sensor itself has a number of novel constructional features. The integral location on a pacing or defibrillation lead yields many benefits. The sensor may also be located, as an alternative, on a separate lead to facilitate easier placement.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An intravascular blood flow sensor comprising:
   (a) a first tube made from a first thermocouple metal having first terminal end and a first thermocouple junction end;
   (b) a second tube made from said first thermocouple metal having a second terminal end and a second thermocouple junction end;
   (c) a third tube made from a second thermocouple metal with a third thermocouple junction end and a fourth thermocouple junction end wherein the first thermocouple junction end is attached to the third thermocouple junction end to form a first thermocouple junction and wherein the second thermocouple junction end is attached to the fourth thermocouple junction end to form a second thermocouple junction;
   (d) a fourth tube made of a material having a predetermined electrical resistance with two heating terminals connected thereto and is substantially surrounded by the second thermocouple junction with an insulating material therebetween; and
   (e) an insulating body surrounding the first second and third tubes to electrically but not thermally insulate the tubes from the blood flow.

2. The intravenous blood flow sensor of claim 1 wherein the first, second and third tubes form a tubular thermocouple which surrounds the fourth tube, wherein the fourth tube is concentrically located within the tubular thermocouple and, further wherein the tubular thermocouple and fourth tube concentrically surround a catheter body.

3. The intravenous blood flow sensor of claim 1 and further including means for sensing the impedance of the blood proximate said blood flow sensor.

4. A cardiac rhythm management device comprising:
   (a) an implantable cardiac tissue stimulator having a predetermined base stimulating rate associated with a first blood flow rate;
   (b) blood flow rate sensing means positionable in the superior vena cava or pulmonary artery and operatively coupled to said stimulator for producing a control signal indicating a departure of blood flow rate from said first blood flow rate, said blood flow rate sensing means including
      (i) a first tube made from a first thermocouple metal having first terminal end and a first thermocouple junction end;
      (ii) a second tube made from said first thermocouple metal having a second terminal end and a second thermocouple junction end;
      (iii) a third tube made from a second thermocouple metal with a third thermocouple junction end and a fourth thermocouple junction end wherein the first thermocouple junction end is attached to the third thermocouple junction end to form a first thermocouple junction and wherein the second thermocouple junction end is attached to the fourth thermocouple junction end to form a second thermocouple junction;
      (iv) a fourth tube made of a material having a predetermined electrical resistance with two heating terminals connected thereto and is substantially surrounded by the second thermocouple junction with an insulating material therebetween; and
      (v) an insulating body surrounding the first second and third tubes to electrically but not thermally insulate the tubes from the blood flow.
   (c) means for applying said control signal to the stimulator for changing the stimulating rate from said base rate.

5. The cardiac rhythm management device as in claim 4 wherein said first blood flow rate is characteristic of a physiologic blood flow rate and the extent of said departure is characteristic of a pathologic blood flow rate.

6. The cardiac rhythm management device as in claim 4 wherein said control signal changes said stimulating rate to maximize blood flow rate in the pulmonary artery.

7. The cardiac rhythm management device as in claim 4 wherein said implantable cardiac tissue stimulator is an automatic implantable cardiac defibrillator and said base stimulating rate is associated with a blood flow rate characteristic of normal sinus rhythm, said control signal initiating shock stimulation to the cardiac tissue.

8. A blood flow sensor comprising:
   (a) an elongated flexible plastic tubular body of generally circular cross-section having a proximal end, a distal end and an outside diameter allowing said body to be routed through the vascular system until said distal end is at a predetermined location;
   (b) a tubular resistance heating element supported by said tubular body proximate said distal end;
   (c) first, second and third tubular thermocouple elements surrounding said tubular body and in axially abutting relationship to define first and second thermocouple junctions therebetween, said second junction overlaying said resistance heating element;
   (d) a layer of electrically insulating, heat conducting material covering said first, second and third thermocouple elements; and
   (e) conductor means routed through said tubular body for applying an electrical current to said resistance heating element and for conveying a voltage signal from said thermocouple elements.

* * * * *